(12) United States Patent
Hanton et al.

(10) Patent No.: US 8,859,696 B2
(45) Date of Patent: Oct. 14, 2014

(54) OLIGOMERISATION OF OLEFINIC COMPOUNDS WITH REDUCED POLYMER FORMATION

(75) Inventors: Martin John Hanton, Fife (GB); David Matthew Smith, Fife (GB); William Fullard Gabrielli, Fife (GB); Mark William Kelly, Bristol (GB)

(73) Assignee: Sasol Technology (PTY) Limited, Johannesburg (ZA)

( * ) Notice: Subject to any disclaimer, the term of this patent is extended or adjusted under 35 U.S.C. 154(b) by 0 days.

(21) Appl. No.: 13/502,664

(22) PCT Filed: Oct. 13, 2010

(86) PCT No.: PCT/IB2010/054631
§ 371 (c)(1),
(2), (4) Date: Aug. 30, 2012

(87) PCT Pub. No.: WO2011/048527
PCT Pub. Date: Apr. 28, 2011

(65) Prior Publication Data
US 2012/0316303 A1 Dec. 13, 2012

(30) Foreign Application Priority Data
Oct. 19, 2009 (ZA) .................................. 2009/07285

(51) Int. Cl.
| C08F 4/00 | (2006.01) |
| C08F 110/02 | (2006.01) |
| C08F 4/69 | (2006.01) |
| C08F 4/52 | (2006.01) |
| C07C 2/32 | (2006.01) |
| C07C 2/36 | (2006.01) |

(52) U.S. Cl.
CPC ............... *C07C 2/36* (2013.01); *C07C 2531/12* (2013.01); *C07C 2/32* (2013.01); *C07C 2531/14* (2013.01); *C07C 2531/24* (2013.01)
USPC ............ 526/133; 502/167; 502/104; 502/102

(58) Field of Classification Search
None
See application file for complete search history.

(56) References Cited

U.S. PATENT DOCUMENTS

| 3,240,773 | A | * | 3/1966 | Boor, Jr. .................... 526/141 |
| 5,221,774 | A | | 6/1993 | Wu |
| 7,285,607 | B2 | | 10/2007 | Blann et al. |
| 2008/0058486 | A1 | | 3/2008 | McCullough et al. |

FOREIGN PATENT DOCUMENTS

| WO | WO 0204119 A1 * | 1/2002 |
| WO | WO 03/053890 A1 | 7/2003 |
| WO | WO 03/053891 A1 | 7/2003 |
| WO | WO 2004/056477 A1 | 7/2004 |
| WO | WO 2004/056478 A1 | 7/2004 |
| WO | WO 2004/056479 A1 | 7/2004 |
| WO | WO 2004/056480 A1 | 7/2004 |
| WO | WO 2005/123633 A1 | 12/2005 |
| WO | WO 2005/123884 A2 | 12/2005 |
| WO | WO 2008/085659 A1 | 7/2008 |

OTHER PUBLICATIONS

International Search Report issued by the Europoean Patent Office in International Application No. PCT/IB2010/054631, mailed Apr. 1, 2011 (2 pages).

* cited by examiner

*Primary Examiner* — Ling Choi
*Assistant Examiner* — Catherine S Branch
(74) *Attorney, Agent, or Firm* — Finnegan Henderson Farabow Garrett & Dunner LLP

(57) ABSTRACT

A process for producing an oligomeric product by oligomerization of at least one olefinic compound, the process including a) providing an activated oligomerization catalyst, by combining, in any order, i) a source of chromium, ii) a ligating compound, iii) a catalyst activator or combination of catalyst activators, b) providing a zinc compound, and c) contacting the at least one olefinic compound with a composition containing the activated oligomerization catalyst and the zinc compound, the zinc compound being present in a sufficient quantity such that the ratio of the molar amount of zinc in the zinc compound to the molar amount of chromium in the source of chromium is between 1 and 10,000. The invention also provides a process of activating an oligomerization catalyst to be used to produce an oligomeric product from at least one olefinic compound.

15 Claims, No Drawings

OLIGOMERISATION OF OLEFINIC COMPOUNDS WITH REDUCED POLYMER FORMATION

TECHNICAL FIELD

This invention relates to the oligomerisation of olefinic compounds in the presence of an activated oligomerisation catalyst and relates further to the use of a zinc compound in oligomerisation.

BACKGROUND ART

A number of different oligomerisation technologies are known to produce α-olefins. Some of these processes, including the Shell Higher Olefins Process and Ziegler-type technologies, have been summarized in WO 04/056479 A1. The same document also discloses that the prior art (e.g. WO 03/053891 and WO 02/04119) teaches that chromium based catalysts containing heteroaromatic ligands with both phosphorus and nitrogen heteroatoms, selectively catalyse the trimerisation of ethylene to 1-hexene.

Processes wherein transition metals and heteroaromatic ligands are combined to form catalysts for trimerisation, tetramerisation, oligomerisation and polymerisation of olefinic compounds have also been described in different patent applications such as WO 03/053890 A1; WO 03/053891; WO 04/056479 A1; WO 04/056477 A1; WO 04/056480 A1; WO 04/056478 A1; WO 05/123884 A2; WO 05/123633 A1 and U.S. Pat. No. 7,285,607.

The catalysts utilized in the abovementioned trimerisation, tetramerisation, oligomerisation or polymerisation processes all include one or more activators to activate the catalyst. Such an activator is a compound that generates an active catalyst when the activator is combined with the catalyst.

Suitable activators include organoaluminium compounds, organoboron compounds, organic salts, such as methyl lithium and methyl magnesium bromide, inorganic acids and salts, such as tetrafluoroboric acid etherate, silver tetrafluoroborate, sodium hexafluoroantimonate and the like.

A common catalyst activator used in combination with Cr based catalysts for oligomerisation of olefinic compounds is alkylaluminoxane, particularly methylaluminoxane (MAO). It is well known that MAO includes significant quantities of alkylaluminium in the form of trimethylaluminium (TMA), and in effect the catalyst activator is a combination of TMA and MAO. The MAO may also be replaced with modified MAO (MMAO), which may contain free trialkylaluminium in the form of TMA and heavier trialkylaluminiums. The use of organoboron compounds as catalyst activators is also known.

Activators containing aluminium compounds are costly to the effect that it impacts significantly on process economics of olefin oligomerisation technologies that utilize this class of activators. For this reason, it is desirable to run commercial oligomerisation processes at low activator concentrations. However, in the case where an aluminium-containing compound was used as an activator for transition metal based oligomerisation catalysts, it was found that at conditions of low starting aluminium concentrations (e.g. <6 mmol/l), low reaction rates and high levels of unwanted solid formation (polyethylene (PE) and waxes) resulted when ethylene was oligomerised.

Reduction in the formation of polymer as a by-product in Cr-based ethylene oligomerisation (both tri- and tetramerisation) processes remains an ongoing challenge, as polymer fouling reduces plant run time and necessitates shut-downs due to blockages.

The inventors of the present invention have found that reductions in polymer formation levels can be achieved in the chromium catalysed olefin oligomerisation processes by the incorporation of a zinc compound, in particular dialkyl zinc, in the catalyst system in the manner described below.

The use of a zinc compound in olefin oligomerisation is not unknown, but it has not been disclosed previously that it may be used in the manner of the present invention to achieve a reduction in polymer formation as herein disclosed. Thus the use of chain transfer reagents within the field of polymerisation has long been known. For example the use of triethylaluminium in combination with various 'chain growth' type polymerisation catalysts (e.g. 1,3,7-triazacyclonanone) has been previously studied.

WO 2008/085659 and US 2008/0058486 both disclose the use of various activators for oligomerisation catalyst systems. Both contain the statement that "(o)ther general activators or compounds useful in an oligomerization reaction may be used. These compounds may be activators in some contexts, but may also serve other functions in the reaction system, such as alkylating a metal center or scavenging impurities. These compounds are within the general definition of "activator," but are not considered herein to be ion-forming activators." Both these publications broadly identify these "other" components as Group 13 reagents, divalent metal reagents, and alkali metal reagents and names diethyl zinc as one of a large group of reagents said to be "useful as activators for the catalyst compounds" with which the publications are concerned. However, neither of these publications exemplify such use of these "other" components and in particular of diethyl zinc, nor do they disclose any benefit derived from the use of diethyl zinc, or any effect that such use of diethyl zinc might have on the extent of polymer formation in chromium catalysed olefin oligomerisation.

DISCLOSURE OF THE INVENTION

According to the present invention, there is provided a process for producing an oligomeric product by the oligomerisation of at least one olefinic compound, the process including:
a) providing an activated oligomerisation catalyst by combining, in any order,
 i) a source of chromium;
 ii) a ligating compound of the formula I $$(R^1)_m X^1(Y) X^2(R^2)_n \qquad \text{I}$$

wherein:
 $X^1$ and $X^2$ are independently an atom selected from the group consisting of nitrogen, phosphorus, arsenic, antimony, bismuth, oxygen, sulphur and selenium or said atom oxidized by S, Se, N or O where the valence of $X^1$ and/or $X^2$ allows for such oxidation;
 Y is a linking group between $X^1$ and $X^2$;
 m and n are independently 0, 1 or a larger integer; and
 $R^1$ and $R^2$ are independently hydrogen, a hydrocarbyl group, an organoheteryl group or a heterohydrocarbyl group, and $R^1$ being the same or different when m>1, and $R^2$ being the same or different when n>1;
 iii) a catalyst activator or combination of catalyst activators;

b) providing a zinc compound; and
c) contacting the at least one olefinic compound with a composition containing the activated oligomerisation catalyst and the zinc compound, the zinc compound being present in a sufficient quantity such that the ratio of the molar amount of zinc in the zinc compound to the molar amount of chromium in the source of chromium is between 1 and 10000.

According to the present invention there is also provided a process for activating an oligomerisation catalyst to be used to produce an oligomeric product from at least one olefinic compound, the process comprising the combination, in any order, of
i) a source of chromium;
ii) a ligating compound of the formula I

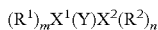

$(R^1)_m X^1 (Y) X^2 (R^2)_n$   I wherein:
$X^1$ and $X^2$ are independently an atom selected from the group consisting of nitrogen, phosphorus, arsenic, antimony, bismuth, oxygen, sulphur and selenium or said atom oxidized by S, Se, N or O where the valence of $X^1$ and/or $X^2$ allows for such oxidation;
Y is a linking group between $X^1$ and $X^2$;
m and n are independently 0, 1 or a larger integer; and
$R^1$ and $R^2$ are independently hydrogen, a hydrocarbyl group an organoheteryl group or a heterohydrocarbyl group, and $R^1$ being the same or different when m>1, and $R^2$ being the same or different when n>1;
iii) a catalyst activator or combination of catalyst activators;
iv) a zinc compound, the zinc compound being present in a sufficient quantity such that the ratio of the molar amount of zinc in the zinc compound to the molar amount of chromium in the source of chromium is between 1 and 10000.

In both the above aspects of the invention the zinc compound is present in the reaction of the invention in a sufficient quantity such that the ratio of the molar amount of zinc in the zinc compound to the molar amount of chromium in the source of chromium is preferably between 10 and 1000, and more preferably between 50 and 450.

The above aspects of the invention further may include the use of a solvent.

In this specification, the following definitions apply:
The term olefinic compound denotes an olefin or any compound which includes a carbon to carbon double bond and olefinic moiety has a corresponding meaning;
A hydrocarbyl group is a univalent group formed by removing one hydrogen atom from a hydrocarbon;
A hydrocarbylene group is a divalent group formed by removing two hydrogen atoms from the same or different carbon atoms in a hydrocarbon, the resultant free valencies of which are not engaged in a double bond;
A heterohydrocarbyl group is a univalent group formed by removing one hydrogen atom from a heterohydrocarbon, that is a hydrocarbon compound which includes at least one hetero atom (that is, not being H or C), and which group binds with other moieties through the resultant free valency on that carbon atom;
A heterohydrocarbylene group is a divalent group formed by removing two hydrogen atoms from the same or different carbon atoms in a heterohydrocarbon, the free valencies of which are not engaged in a double bond and which group binds with other moieties through the resultant free valencies on that or those carbon atoms;

An organoheteryl group is a univalent group containing carbon atoms and at least one hetero atom, and which has its free valence at an atom other than carbon;
A polar substituent is a substituent with a permanent electric or induced dipole moment; and
A non-polar substituent is a substituent without a permanent electric or induced dipole moment.

The oligomerisation catalyst of the present invention is preferably a trimerisation catalyst or a tetramerisation catalyst.

The oligomerisation process for producing an oligomeric product is preferably a trimerisation process for producing a trimeric product by the utilization of a trimerisation catalyst or a tetramerisation process for producing a tetrameric product by utilization of a tetramerisation catalyst.

The inventors of the present invention have surprisingly found that the incorporation of a zinc compound in the process described above, results in a reduction in solids formation, that is, polymer and in particular polyethylene formation relative to processes in which such zinc compound is absent.

Oligomerisation Catalyst
Source of Chromium (i):
The source of chromium may be an inorganic salt, an organic salt, a coordination compound or an organometallic complex.

Preferably the source of chromium is selected from the group consisting of chromium trichloride tris-tetrahydrofuran complex; (benzene)tricarbonyl chromium; chromium (III) octanoate; chromium hexacarbonyl; chromium (III) acetylacetonate, chromium (III) naphthenate, chromium (III) 2-ethylhexanoate, chromium (III) acetate, chromium (III) 2,2,6,6-tetramethylheptadionate, chromium (III) chloride. Preferably it is chromium (III) acetylacetonate or chromium (III) 2-ethylhexanoate.

Ligating Compound (ii):
$X^1$ and/or $X^2$ are preferably independently phosphorus or phosphorus oxidised by S or Se or N or O. Preferably $X^1$ and $X^2$ are the same, and most preferably both are P.

It will be appreciated that m and n are dependent on factors such as the valence and oxidation state of $X^1$ and $X^2$, bond formation of Y with $X^1$ and $X^2$ respectively, and bond formation of $R^1$ and $R^2$ with $X^1$ and $X^2$ respectively. Preferably both m and n are not 0.

Preferably the ligating compound is a bidentate ligand.
Preferably the ligating compound is of the formula II

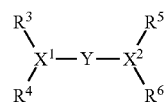

wherein Y is as defined herein, $X^1$ and $X^2$ are independently selected from the group consisting of nitrogen, phosphorus, arsenic, antimony and bismuth and $R^3$ to $R^6$ are each independently a hydrocarbyl group or a heterohydrocarbyl group.

Preferably $X^1$ and $X^2$ are independently selected from the group consisting of phosphorus and nitrogen. More preferably $X^1$ and $X^2$ are the same. Most preferably both $X^1$ and $X^2$ are phosphorus.

$R^3$ to $R^6$ may be independently selected from the group consisting of a non-aromatic moiety; an aromatic moiety; and a heteroaromatic moiety. Preferably each of $R^3$ to $R^6$ is an aromatic or heteroaromatic moiety, more preferably an aromatic moiety (including a substituted aromatic moiety). The aromatic moiety (or substituted aromatic moiety) may comprise phenyl or a substituted phenyl.

One or more of $R^3$ to $R^6$ may be a substituted hydrocarbyl group or a substituted heterohydrocarbyl group, of which at least one substituent is bound to a hydrocarbyl group or a heterohydrocarbyl group.

In this specification, a substituent with reference to moieties bound to $X^1$ and/or $X^2$ is a moiety (excluding H) that is bound to a linear structure or a cyclic structure bound to $X^1$ and/or $X^2$, but the substituent does not form part of the linear or cyclic structure.

The linear or cyclic structure may be selected from the group consisting of a linear hydrocarbyl, a linear heterohydrocarbyl, a cyclic hydrocarbyl and a cyclic heterohydrocarbyl group. Linear hydrocarbyl may include methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl and decynyl.

Linear heterohydrocarbyl may include methoxy, ethoxy, thiomethoxy, thioethoxy, methylsilyl, ethylsilyl, methylamino, methylphosphino, methoxymethyl and thiomethoxymethyl. Cyclic hydrocarbyl may include cyclopropyl, cyclobutyl, cyclopentyl, cyclohexyl, cycloheptyl, cyclooctyl, cyclononyl, cyclodecyl, cyclopentenyl, cyclohexenyl, cyclo-octenyl, phenyl, cyclopentadienyl, naphthaleneyl, norbornyl, adamantyl, phenanthreneyl, anthraceneyl, phenaleneyl, tetrahydronaphthaleneyl, decalinyl, indenyl and tetrahydroindenyl. Cyclic heterohydrocarbyl may include tetrahydrofuranyl, tetrahydrothiopheneyl, pyrrolideneyl, piperidineyl, pyrrolineyl, oxazolyl, thiazolyl, furanyl, thiopheneyl, pyrazolinyl, pyrazolyl, imidazolyl, benzofuranyl, coumaranyl and indolyl.

$R^3$ to $R^6$ may also be selected from a group of metallocenes such as a ferroceneyl, zirconoceneyl and titanoceneyl group.

Preferably $R^3$ to $R^6$ are aromatic moieties of which a ring atom of the aromatic ring structure is bound to either $X^1$ or $X^2$ and with a polar substituent bound to a ring atom of the aromatic ring structure adjacent to the ring atom bound to $X^1$ or $X^2$.

Preferably, if two or more of $R^3$ to $R^6$ are aromatic moieties with a ring atom of the aromatic ring structure bound to either $X^1$ and $X^2$ not more than two of said aromatic moieties $R^3$ and $R^6$ have a substituent bound to a ring atom of the aromatic ring structure adjacent to the ring atom bound to $X^1$ or $X^2$.

In one embodiment of the invention, $R^3$ to $R^6$ are the same or different and each is a hydrocarbyl group, or a heterohydrocarbyl group which contains no substituent or contains a non-polar substituent. Preferably each of $R^3$ to $R^6$ does not include any polar substituent. In one embodiment of the invention at least two of (but preferably all of) $R^3$ to $R^6$ are aromatic moieties with a ring atom of the aromatic ring structure bound to $X^1$ or $X^2$, but preferably not more than two of said aromatic moieties $R^3$ to $R^6$ have a non-polar substituent other than H bound to a ring atom of the aromatic ring structure adjacent to the ring atom bound to $X^1$ or $X^2$.

Preferably none of the aromatic moieties $R^3$ to $R^6$ have a non-polar substituent bound to a ring atom of the aromatic ring structure adjacent to the ring atom bound to $X^1$ or $X^2$. Preferably all of aromatic moieties $R^3$ to $R^6$ are non-substituted aromatic moieties.

Examples of suitable non-polar substituents include, but are not limited to, methyl, ethyl, ethenyl, propyl, iso-propyl, cyclopropyl, propenyl, propynyl, butyl, sec-butyl, tertiary-butyl, cyclobutyl, butenyl, butynyl, pentyl, isopentyl, neopentyl, cyclopentyl, pentenyl, pentynyl, hexyl, sec-hexyl, cyclohexyl, 2-methylcyclohexyl, 2-ethylcyclohexyl, 2-isopropylcyclohexyl, cyclohexenyl, hexenyl, hexynyl, octyl, cyclo-octyl, cyclo-octenyl, decyl, benzyl, phenyl, tolyl, xylyl, o-methylphenyl, o-ethylphenyl, o-isopropylphenyl, o-t-butylphenyl, cumyl, mesityl, biphenyl, naphthyl, anthracenyl, and the like.

Any one of $R^3$ to $R^6$ may be independently linked to one or more of each other, or to Y to form a cyclic structure.

$R^3$ and $R^4$ may be the same and $R^5$ and $R^6$ may be the same. $R^3$ to $R^6$ may all be the same.

In another embodiment of the invention, $R^3$ to $R^6$ are the same or different and each is a hydrocarbyl group, or a heterohydrocarbyl group (preferably an organyl group), provided that at least one of $R^3$ to $R^6$ contains a polar substituent on a carbon atom, but not one of $R^3$ to $R^6$ contains a polar substituent on a carbon atom of $R^3$ to $R^6$ adjacent to a carbon atom bound to $X^1$ or $X^2$. One or more or all of $R^3$ to $R^6$ may be independently selected from the group consisting of a substituted non-aromatic moiety; a substituted aromatic moiety; and a substituted heteroaromatic moiety. Preferably each of $R^3$ to $R^6$ is a substituted aromatic or a substituted heteroaromatic moiety, more preferably a substituted aromatic moiety. The substituted aromatic moiety may comprise a substituted phenyl. In one embodiment of the invention at least two of (but preferably all of) $R^3$ to $R^6$ are aromatic with a ring atom of the aromatic ring structure bound to $X^1$ or $X^2$, but preferably not more than two of said aromatic moieties $R^3$ to $R^6$ have a substituent bound to a ring atom of the aromatic ring structure adjacent to the ring atom bound to $X^1$ or $X^2$.

Any polar substituent on one or more of $R^3$, $R^4$, $R^5$ and $R^6$ may be electron donating.

Suitable polar substituents may be a methoxy, ethoxy, isopropoxy, $C_3$-$C_{20}$ alkoxy, phenoxy, methoxymethyl, methylthiomethyl, 1,3-oxazolyl, methoxymethoxy, hydroxyl, amino, pentafluorophenoxy, tosyl, methylsulfanyl, trimethylsiloxy, dimethylamino, sulphate, nitro, halides or the like.

Y may be selected from the group consisting of an organic linking group such as a hydrocarbylene, substituted hydrocarbylene, heterohydrocarbylene and a substituted heterohydrocarbylene; an inorganic linking group comprising either a single- or two-atom linker spacer; and a group comprising methylene; dimethylmethylene; ethylene; ethene-1,2-diyl; propane-1,2-diyl, propane-1,3-diyl; cyclopropane-1,1-diyl; cyclopropane-1,2-diyl; cyclobutane-1,2-diyl, cyclopentane-1,2-diyl, cyclohexane-1,2-diyl, cyclohexane-1,1-diyl; 1,2-phenylene; naphthalene-1,8-diyl; phenanthrene-9,10-diyl, phenanthrene-4,5-diyl, 1,2-catecholate, 1,2-diarylhydrazine-1,2-diyl (—N(Ar)—N(Ar)—) where Ar is an aryl group; 1,2-dialkylhydrazine-1,2-diyl (—N(Alk)-N(Alk)-) where Alk is an alkyl group; —B($R^7$)—, —Si($R^7$)$_2$—, —P($R^7$)— and —N($R^7$)— where $R^7$ is hydrogen, a hydrocarbyl or heterocarbyl or halogen.

Preferably, Y may be —N($R^7$)— and $R^7$ may be selected from the group consisting of hydrogen, alkyl, substituted alkyl, aryl, substituted aryl, aryloxy, substituted aryloxy, halogen, alkoxycarbonyl, carbonyloxy, alkoxy, aminocarbonyl, carbonylamino, dialkylamino, silyl groups or derivatives thereof, and aryl substituted with any of these substituents. Preferably $R^7$ may be a hydrocarbyl or a heterohydrocarbyl or an organoheteryl group. $R^7$ may be methyl, ethyl, propyl, isopropyl, cyclopropyl, allyl, butyl, tertiary-butyl, sec-butyl, cyclobutyl, pentyl, isopentyl, 1,2-dimethylpropyl (3-methyl-2-butyl), 1,2,2-trimethylpropyl (R/S-3,3-dimethyl-2-butyl), 1-(1-methylcyclopropyl)-ethyl, neopentyl, cyclopentyl, cyclohexyl, cycloheptyl, cyclo-octyl, decyl, cyclodecyl, 1,5-dimetylheptyl, 1-methylheptyl, 2-naphthylethyl, 1-naphthylmethyl, adamantylmethyl, 1-adamantyl, 2-adamantyl, 2-isopropylcyclohexyl, 2,6-dimethylcyclohexyl, cyclododecyl, 2-methylcyclohexyl, 3-methylcyclohexyl, 4-methylcyclohexyl, 2-ethylcyclohexyl, 2-isopropylcyclohexyl, 2,6-dimethyl-cyclohexyl, exo-2-norbornanyl, isopinocamphenyl, dimethylamino, phthalimido, pyrrolyl, trimethylsilyl, dimethyl-tertiary-butylsilyl, 3-trimethoxylsilane-propyl, indanyl, cyclohexanemethyl, 2-methoxyphenyl, 3-methoxyphenyl, 4-methoxyphenyl, 4-tertiary-butylphenyl, 4-nitrophenyl, (1,1'-bis(cyclohexyl)-4,4'-methylene), 1,6-hexylene, 1-naphthyl, 2-naphthyl, N-morpholine, diphenylmethyl, 1,2-diphenyl-ethyl, phenylethyl, 2-methylphenyl, 3-methylphenyl, 4-methylphenyl, 2,6-dimethyl-phenyl, or a 1,2,3,4-tetrahydronaphthyl.

Preferably the ligating compound is of the formula III

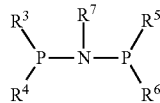

with $R^3$ to $R^7$ as defined above.

Preferably each of $R^3$ to $R^6$ is an alkyl (preferably methyl, ethyl or isopropyl) or aromatic (preferably phenyl or substituted phenyl).

The ligating compound may include a polymeric moiety to render the reaction product of the source of chromium and the said ligating compound to be soluble at higher temperatures and insoluble at lower temperatures e.g. 25° C. This approach may enable the recovery of the complex from the reaction mixture for re-use and has been used for other catalyst as described by D. E. Bergbreiter et al., *J. Am. Chem. Soc.*, 1987, 109, 177-179. In a similar vein these chromium catalysts can also be immobilised by binding the ligating compound to silica, silica gel, polysiloxane or alumina backbone as, for example, demonstrated by C. Yuanyin et al., *Chinese J. React. Pol.*, 1992, 1(2), 152-159 for immobilising platinum complexes.

The ligating compound may include multiple ligating units or derivatives thereof. Non-limiting examples of such ligands include dendrimeric ligands as well as ligands where the individual ligating units are coupled either via one or more of the R groups or via the linking group Y. More specific, but not limiting, examples of such ligands may include 1,2-di-(N(P(phenyl)$_2$)$_2$)-benzene, 1,4-di-(N(P(P$_{phenyl}$)$_2$)$_2$)-benzene, N(CH$_2$CH$_2$N(P(phenyl)$_2$)$_2$)$_3$, 1,4-di-(P(phenyl)N(methyl)P(phenyl)$_2$)-benzene, 1,2-di-(N(P(p-methoxyphenyl)$_2$)$_2$)-benzene, 1,4-di-(N(P(p-methoxyphenyl)$_2$)$_2$)-benzene, N(CH$_2$CH$_2$N(P(p-methoxyphenyl)$_2$)$_2$)$_3$ and 1,4-di-(P(p-methoxyphenyl)N(methyl) P(p-methoxyphenyl)$_2$)-benzene.

The ligating compounds may be prepared using procedures known to one skilled in the art and procedures forming part of the state of the art.

The oligomerisation catalyst may be prepared in situ, that is in the reaction mixture in which the oligomerisation reaction is to take place. Often the oligomerisation catalyst will be prepared in situ. Alternatively the catalyst may be pre-formed or partly pre-formed.

Activation

Activator (iii)

The catalyst activator may be a compound that generates an active catalyst when the activator is combined with the source of chromium and the ligating compound.

In one form of the invention the activator is an organoboron compound that includes a cation and a non-coordinating anion of the general formula

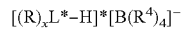

wherein:
L* is an atom selected from the group consisting of N, S and P;
the cation $[(R)_xL^*-H]^+$ is a Bronsted acid;
x is an integer 1, 2 or 3;
each R is the same or different and each is a —H, hydrocarbyl group or a heterohydrocarbyl group;
provided that at least one of R comprises at least 6 carbon atoms and provided further that the total number of carbon atoms in $(R)_x$ collectively is greater than 12;
$R^4$ independently at each occurrence is selected from the group consisting of hydride, dialkylamido, halide, alkoxide, aryloxide, hydrocarbyl, halosubstituted-hydrocarbyl radicals, halosubstituted-alkoxide, halosubstituted-aryloxide and a halosubstituted aromatic moiety with at least one halide substituent on the aromatic moiety.

$[(R)_xL^*-H]^+$ is a cation. More particularly, $[(R)_xL^*-H]^+$ is a Bronsted acid. A Bronsted acid is any compound that is capable of donating a hydrogen ion (proton).

Where L* is an atom selected from the group consisting of N or P, the cation $[(R)_xL^*-H]^+$ may be represented by the formula

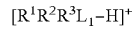

wherein:
$L_1$=N or P;
$R^1$, $R^2$ and $R^3$ are the same or different and each is a —H, hydrocarbyl group or a heterohydrocarbyl group; and
provided that at least one of $R^1$, $R^2$ and $R^3$ comprises at least 6 carbon atoms and provided further that the total number of carbon atoms in $R^1$, $R^2$ and $R^3$ collectively is greater than 12.

Where L* is S, the cation $[(R)_xL^*-H]^+$ may be represented by the formula

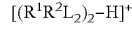

wherein:
$L_2$=S;
$R^1$ and $R^2$ are the same or different and each is a —H, hydrocarbyl group or a heterohydrocarbyl group; and
provided that at least one of $R^1$ and $R^2$ comprises at least 6 carbon atoms and provided further that the total number of carbon atoms in $R^1$ and $R^2$ collectively is greater than 12.

$R^1$, $R^2$ and $R^3$ are each independently an aliphatic hydrocarbyl or an aliphatic heterohydrocarbyl group, preferably a saturated aliphatic hydrocarbyl or a saturated aliphatic heterohydrocarbyl, more preferably a substituted hydrocarbyl or a substituted heterohydrocarbyl where the substituents may be non-polar groups.

Suitable examples of $R^1$, $R^2$ and $R^3$ include, but are not limited to, methyl, ethyl, ethylenyl, propyl, propenyl, propynyl, butyl, pentyl, hexyl, cyclohexyl, 2-methylcyclohexyl, 2-ethylcyclohexyl, octyl, 2-ethylhexyl, iso-octyl, decyl, dodecyl, tetradecyl, octadecyl, 2-isopropylcyclohexyl, benzyl, phenyl, tolyl, xylyl, o-methylphenyl, o-ethylphenyl, o-isopropylphenyl, o-t-butylphenyl, biphenyl, naphthyl and the like.

Examples of suitable non-polar substituents include, but are not limited to, butyl, pentyl, hexyl, sec-hexyl, cyclohexyl, 2-methylcyclohexyl, 2-ethylcyclohexyl, 2-isopropylcyclohexyl, cyclohexenyl, hexenyl, hexynyl, octyl, cyclo-octyl, cyclo-octenyl, 2-ethylhexyl, iso-octyl, decyl, benzyl, phenyl, tolyl, xylyl, o-methylphenyl, o-ethylphenyl, o-isopropylphenyl, o-t-butylphenyl, cumyl, mesityl, biphenyl, naphthyl, anthracenyl, and the like.

In one embodiment of the invention, at least one of R comprises 6 to 40 carbon atoms with a total of from 13 to 100 carbons. Preferably, at least one of R comprises 6 to 40 carbon atoms with a total of from 21 to 90 total carbons.

It is believed that the presence of long chain hydrocarbon substituents, that is hydrocarbon substituents having at least 6 carbon atoms, renders the activator more soluble in aliphatic solutions thereby facilitating activation of the catalyst. Moreover, it is believed that where the total number of carbon atoms in the hydrocarbyl substituents that $R^1$, $R^2$ and $R^3$ have is greater than 12, the solubility of the catalyst activator in aliphatic compounds will be increased thereby resulting in improved olefin oligomerisation with low solid formation.

As discussed herein above, $R^4$ may be a halosubstituted aromatic moiety with at least one halide substituent on the aromatic ring. In a preferred embodiment of the invention, the halosubstituted aromatic moiety is pentafluorophenyl.

Illustrative, but non-limiting examples of organoboron compounds having a cation and a non-coordinating anion of the formula of the present invention, set out herein above, include dihexyl(methyl)ammonium tetrakis(pentafluorophenyl) borate;
dioctyl(methyl)ammonium tetrakis(pentafluorophenyl) borate;
methyldi(octyl)ammonium tetrakis(pentafluorophenyl) borate;
decyldi(methyl)ammonium tetrakis(pentafluorophenyl) borate;
dodecyldi(methyl)ammonium tetrakis(pentafluorophenyl) borate;
tetradecyldi(methyl)ammonium tetrakis(pentafluorophenyl) borate;
hexaadecyldi(methyl)ammonium tetrakis(pentafluorophenyl) borate;
octadecyldi(methyl)ammonium tetrakis(pentafluorophenyl) borate;
eicosyldi(methyl)ammonium tetrakis(pentafluorophenyl) borate;
methyldi(decyl)ammonium tetrakis(pentafluorophenyl) borate;
methyldi(dodecyl)ammonium tetrakis(pentafluorophenyl) borate;
methyldi(tetradecyl)ammonium tetrakis(pentafluorophenyl) borate;
methyldi(hexadecyl)ammonium tetrakis(pentafluorophenyl) borate;
methyldi(octadecyl)ammonium tetrakis(pentafluorophenyl) borate;
methyldi(eicosyl)ammonium tetrakis(pentafluorophenyl) borate;
trihexylammonium tetrakis(pentafluorophenyl) borate;
trioctylammonium tetrakis(pentafluorophenyl) borate;
tri(2-ethylhexyl)ammonium tetrakis(pentafluorophenyl) borate;
tri(iso-octyl)ammonium tetrakis(pentafluorophenyl) borate;
tridecylammonium tetrakis(pentafluorophenyl) borate;
tridodecylammonium tetrakis(pentafluorophenyl) borate;
tritetradecylammonium tetrakis(pentafluorophenyl) borate;
trihexadecylammonium tetrakis(pentafluorophenyl) borate;
trioctadecylammonium tetrakis(pentafluorophenyl) borate;
trieicosylammonium tetrakis(pentafluorophenyl) borate;
hexyldi(n-butyl)ammonium tetrakis(pentafluorophenyl) borate;
octyldi(n-butyl)ammonium tetrakis(pentafluorophenyl) borate;
decyldi(n-butyl)ammonium tetrakis(pentafluorophenyl) borate;
dodecyldi(n-butyl)ammonium tetrakis(pentafluorophenyl) borate;
octadecyldi(n-butyl)ammonium tetrakis(pentafluorophenyl) borate;
N,N-dihexylanilinium tetrakis(pentafluorophenyl) borate;
N,N-dioctylanilinium tetrakis(pentafluorophenyl) borate;
N,N-didodecylanilinium tetrakis(pentafluorophenyl) borate;
N-methyl-N-dodecylanilinium tetrakis(pentafluorophenyl) borate;
N,N-di(octadecyl)(2,4,6-trimethylanilinium) tetrakis(pentafluorophenyl) borate;
cyclohexyldi(dodecyl)ammonium tetrakis(pentafluorophenyl)borate;
methyldi(dodecyl)ammonium tetrakis-(2,3,4,6-tetrafluorophenyl) borate;
trioctylphosphonium tetrakis(pentafluorophenyl) borate;
trihexylphosphonium tetrakis(pentafluorophenyl) borate;
tributylphosphonium tetrakis(pentafluorophenyl) borate;
dioctyl(methyl)phosphonium tetrakis(pentafluorophenyl) borate;
dimethyl(octyl)phosphonium tetrakis(pentafluorophenyl) borate;
bis(dihexylsulfide)onium tetrakis(pentafluorophenyl) borate, $[\{(C_6H_{13})_2S\}_2H][B(C_6F_5)_4]$;
bis(dioctylsulfide)onium tetrakis(pentafluorophenyl) borate, $[\{(C_8H_{17})_2S\}_2H][B(C_6F_5)_4]$;
bis(didecylsulfide)onium tetrakis(pentafluorophenyl) borate, $[\{(C_{10}H_{21})_2S\}_2H][B(C_6F_5)_4]$; and
bis(didodecylsulfide)onium tetrakis(pentafluorophenyl) borate, $[\{(C_{12}H_{25})_2S\}_2H][B(C_6F_5)_4]$.

The source of chromium and the organoboron compound may be combined in proportions to provide organoboron compound/chromium molar ratios from about 0.1 to 50 organoboron to 1 chromium, preferably from about 0.8 to 20 organoboron to 1 chromium, and more preferably from 1 to 10 organoboron to 1 chromium.

Preferably the concentration of the boron in the activated catalyst prior to dilution is at least 0.01 mmol/l. Preferably, the concentration of the boron is 0.1-100 mmol/l, and most preferably the concentration is 0.1-10 mmol/l.

Further non-limiting examples of activators, include alumoxanes, aluminum alkyls, other metal or main group alkyl or aryl compounds, ionizing activators, which may be neutral or ionic, Lewis acids, reducing agents, oxidizing agents, and combinations thereof. In one embodiment, aluminoxane activators are utilized as an activator in the compositions useful in the invention. Aluminoxanes are generally oligomeric compounds containing —Al(R*)—O— sub-units, where R* is an alkyl group. Examples of alumoxanes include methylalumoxane (MAO), ethylalumoxane, isobutylalumoxane, and modified methylalumoxanes (MMAO), which include alkyl groups other than methyl such as ethyl, isobutyl, and n-octyl. Alkylalumoxanes and modified alkylalumoxanes are suitable as catalyst activators, particularly when the abstractable ligand of the catalyst is a halide, alkoxide or amide. Mixtures of different alumoxanes and modified alumoxanes may also be used. The activator compounds comprising Lewis-acid activators and in particular alumoxanes are specifically characterized by the following general formulae:

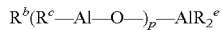

where $R^a$, $R^b$, $R^c$ and $R^e$ are, independently a $C_1$-$C_{30}$ alkyl radical, for example, methyl, ethyl, propyl, butyl, pentyl, hexyl, heptyl, octyl, nonyl, decyl, and "p" is an integer from 1 to about 50. Most specifically, $R^a$, $R^b$, $R^c$ and $R^d$ are each methyl and "p" is a least 4. When an alkyl aluminum halide or alkoxide is employed in the preparation of the alumoxane, one or more $R^e$, $R^b$, $R^c$ or $R^e$ are groups may be halide or alkoxide.

It is recognized that alumoxane is not a discrete material. An alumoxane is generally a mixture of both the linear and cyclic compounds. A typical alumoxane will contain free trisubstituted or trialkyl aluminum, bound trisubstituted or trialkyl aluminum, and alumoxane molecules of varying degree of oligomerisation. For some embodiments, it is preferred that methylalumoxanes contain lower levels of trimethylaluminum. Lower levels of trimethylaluminum can be achieved by reaction of the trimethylaluminum with a Lewis base or by vacuum distillation of the trimethylaluminum or by any other means known in the art.

For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0561476A1, EP 0279586B1, EP 0516476A1, EP 0594218A1 and WO 94/10180.

When the activator is an alumoxane (modified or unmodified), some embodiments select the maximum amount of activator at a 5000-fold molar excess Al/Cr over the catalyst precursor. The minimum preferred activator-to-catalyst-precursor is a 1:1 molar ratio. More specifically, the Al/Cr ratio is from 1000:1 to 100:1.

Alumoxanes may be produced by the hydrolysis of the respective trialkylaluminum compound. MMAO may be produced by the hydrolysis of trimethylaluminum and a higher trialkylaluminum such as triisobutylaluminium.

There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP 0561476A1, EP 0279586B1, EP 0594218A1 and EP 0586665B1, and PCT publications WO 94/10180 and WO 99/15534, all of which are herein fully incorporated by reference.

Aluminum alkyl or organoaluminum compounds which may be utilized as activators (or scavengers) include trimethylaluminum, triethylaluminum, triisobutylaluminum, tri-n-hexylaluminum, tri-n-octylaluminum, diisobutylaluminum hydride, ethylaluminum dichlohde, diethylaluminum chloride, diethylaluminum ethoxide and the like.

Ionizing Activators

In some embodiments, the activator includes compounds that may abstract a ligand making the metal complex cationic and providing a charge-balancing non-coordinating or weakly coordinating anion. The term "non-coordinating anion" (NCA) means an anion which either does not coordinate to said cation or which is only weakly coordinated to said cation thereby remaining sufficiently labile to be displaced by a Lewis base (for example, a neutral Lewis base).

It is within the scope of this invention to use an ionizing or stoichiometric activator, neutral or ionic, such as tri(n-butyl) ammonium tetrakis(pentafluorophenyl)borate, a tris(pentafluorophenyl)boron metalloid precursor or a tris(heptafluoronaphthyl)boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. In some embodiments, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). In other embodiments, the three groups are alkyls having 1 to 4 carbon groups, phenyl, naphthyl or mixtures thereof. In further embodiments, the three groups are halogenated, specifically fluorinated, aryl groups. In even further embodiments, the neutral stoichiometric activator is tris(perfluorophenyl) boron or tris(perfluoronaphthyl) boron.

Ionic stoichiometric activator compounds may contain an active proton, or some other cation associated with, but not coordinated to, or only loosely coordinated to, the remaining ion of the ionizing compound. Such compounds and the like are described in European publications EP 0570982A1, EP 0520732A1, EP 0495375A1, EP 0500944B1, EP 0277003A1 and EP 0277004A1, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a Cr compound with some neutral Lewis acids, such as $B(C_6F_5)_3$, which upon reaction with the abstractable ligand (X) of the Cr compound forms an anion, such as $[B(C_6F_5)_3(X)]^-$, which stabilizes the cationic Cr species generated by the reaction. The catalysts can be prepared with activator components, which are ionic compounds or compositions.

In some embodiments, compounds useful as an activator component in the preparation of the ionic catalyst systems used in the process of this invention comprise a cation, which is optionally a Brönsted acid capable of donating a proton, and a compatible non-coordinating anion which is capable of stabilizing the active catalyst species which is formed when the two compounds are combined and said anion will be sufficiently labile to be displaced by olefinic substrates or other neutral Lewis bases such as ethers, nitrites and the like. Two classes of compatible non-coordinating anions useful herein have been disclosed in EP 0277003A1 and EP 0277004A1 published 1988: anionic coordination complexes comprising a plurality of lipophilic radicals covalently coordinated to and shielding a central charge-bearing metal or metalloid core; and, anions comprising a plurality of boron atoms such as carboranes, metallacarboranes and boranes.

In one preferred embodiment, the stoichiometric activators include a cation and an anion component, and may be represented by the following formula:

$$(L-H)^{d+}(A^{d-})$$

where L is a neutral Lewis base; H is hydrogen; $(L-H)^+$ is a Bronsted acid; $A^{d-}$ is a non-coordinating anion having the charge $d^-$; and d is an integer from 1 to 3.

The cation component, $(L-H)^{d+}$ may include Brönsted acids such as protons or protonated Lewis bases or reducible Lewis acids capable of protonating or abstracting a moiety, such as an alkyl or aryl, from the bulky ligand chromium catalyst precursor, resulting in a cationic transition metal species.

The activating cation $(L-H)^{d+}$ may be a Brönsted acid, capable of donating a proton to the transition metal catalytic precursor resulting in a transition metal cation, including ammoniums, oxoniums, phosphoniums, silyliums, and mixtures thereof, specifically ammoniums of methylamine, aniline, dimethylamine, diethylamine, N-methylaniline, diphenylamine, trimethylamine, triethylamine, N,N-dimethylaniline, methyldiphenylamine, pyridine, p-bromo-N,N-dinnethylaniline, p-nitro-N,N-dimethylaniline, phosphoniums from thethylphosphine, thphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene, and mixtures thereof. The activating cation $(L-H)_d^+$ may also be a moiety such as silver, tropylium, carbeniums, ferroceniums and mixtures, specifically carboniums and ferroceniums. In one embodiment $(L-H)^{d+}$ can be triphenyl carbonium.

The anion component $A^{d-}$ includes those having the formula $(M^{k+}Q_n)^{d-}$ wherein k is an integer from 1 to 5; n is an integer from 2-6; n–k=d; M is an element selected from Group 13 of the Periodic Table of the Elements, specifically boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Specifically, each Q is a fluorinated hydrocarbyl group having 1 to 20 carbon atoms, more specifically each Q is a fluorinated aryl group, and most specifically each Q is a pentafluoryl aryl group. Examples of suitable $A^{d-}$ also include diboron compounds as disclosed in U.S. Pat. No. 5,447,895, which is fully incorporated herein by reference.

In one embodiment of the invention $(M^{k+}Q_n)^{d-}$ may be selected from the group containing the anion $[Al(OR)_4]^-$, a compound including a moiety $Al(OR)_3$ and a salt containing the anion $[Ta(OR)_6]^-$ wherein R is defined as above.

In one embodiment of the invention $(M^{k+}Q_n)^{d-}$ may be selected from the group consisting of $Al(OC_6F_5)_3$; $[Al\{OC(CF_3)_3\}_4]^-$; $[Al(OC_6F_5)_4]^-$; $[Al(C_6F_4O_2)_2]^-$ $[Al\{OC(CF_3)_2C(CF_3)_2O\}_2]$; $[AlF\{OC(CF_3)_3\}_3]$; $[Al_2F\{OC(CF_3)_3\}_6]$; $(Z)Al\{OCH(C_6F_5)_2\}_3$; $(Z)Al\{OC(CF_3)_3\}_3$ and $[Ta(OC_6F_5)_6]^-$ which moiety Z is not-AR as defined above.

Illustrative, but not limiting examples of boron compounds which may be used as a catalyst activator in the preparation of the improved catalysts of this invention are tri-substituted ammonium salts such as:
trimethylammonium tetraphenyl borate,
triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate,
N,N-dimethyl-(2,4,6-trimethylanilinium) tetraphenylborate,
tropillium tetraphenylborate,
triphenylcarbenium tetraphenylborate,
triphenylphosphonium tetraphenylborate,
triethylsilylium tetraphenylborate,
benzene(diazonium)tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl-(2,4,6-trimethylanilinium) tetrakis(pentafluorophenyl)borate,
tropillium tetrakis(pentafluorophenyl)borate,
triphenylcarbenium tetrakis(pentafluorophenyl)borate,
triphenylphosphonium tetrakis(pentafluorophenyl)borate,
triethylsilylium tetrakis(pentafluorophenyl)borate,
benzene(diazonium) tetrakis(pentafluorophenyl)borate,
trimethylammonium tetrakis-(2,3,4,6-tetrafluorophenyl) borate,
triethylammonium tetrakis-(2,3,4,6-tetrafluorophenyl)borate,
tripropylammonium tetrakis-(2,3,4,6-tetrafluorophenyl)borate,
tri(n-butyl)ammonium tetrakis-(2,3,4,6-tetrafluoro-phenyl)borate,
dimethyl(t-butyl)ammonium tetrakis-(2,3,4,6-tetrafluorophenyl)borate,
N,N-dimethylanilinium tetrakis-(2,3,4,6-tetrafluorophenyl)borate,
N,N-diethylanilinium tetrakis-(2,3,4,6-tetrafluorophenyl)borate,
N,N-dimethyl-(2,4,6-trimethylanilinium) tetrakis-(2,3,4,6-tetrafluorophenyl)borate,
tropillium tetrakis-(2,3,4,6-tetrafluorophenyl)borate,
triphenylcarbenium tetrakis-(2,3,4,6-tetrafluorophenyl)borate,
triphenylphosphonium tetrakis-(2,3,4,6-tetrafluorophenyl)borate,
triethylsilylium tetrakis-(2,3,4,6-tetrafluorophenyl)borate,
benzene(diazonium) tetrakis-(2,3,4,6-tetrafluorophenyl)borate,
trimethylammonium tetrakis(perfluoronaphthyl)borate,
triethylammonium tetrakis(perfluoronaphthyl)borate,
tripropylammonium tetrakis(perfluoronaphthyl)borate,
tri(n-butyl)ammonium tetrakis(perfluoronaphthyl)borate,
tri(t-butyl)ammonium tetrakis(perfluoronaphthyl)borate,
N,N-dimethylanilinium tetrakis(perfluoronaphthyl)borate,
N,N-diethylanilinium tetrakis(perfluoronaphthyl)borate,
N,N-dimethyl-(2,4,6-trimethylanilinium) tetrakis(perfluoronaphthyl)borate,
tropillium tetrakis(perfluoronaphthyl)borate,
triphenylcarbenium tetrakis(perfluoronaphthyl)borate,
triphenylphosphonium tetrakis(perfluoronaphthyl)borate,
triethylsilylium tetrakis(perfluoronaphthyl)borate,
benzene(diazonium) tetrakis(perfluoronaphthyl)borate,
trimethylammonium tetrakis(perfluorobiphenyl)borate,
triethylammonium tetrakis(perfluorobiphenyl)borate,
tripropylammonium tetrakis(perfluorobiphenyl)borate,
tri(n-butyl)ammonium tetrakis(perfluorobiphenyl)borate,
tri(t-butyl)ammonium tetrakis(perfluorobiphenyl)borate,
N,N-dimethylanilinium tetrakis(perfluorobiphenyl)borate,
N,N-diethylanilinium tetrakis(perfluorobiphenyl)borate, N,N-dimethyl-(2,4,6-trimethylanilinium) tetrakis(perfluorobiphenyl)borate,
tropillium tetrakis(perfluorobiphenyl)borate,
triphenylcarbenium tetrakis(perfluorobiphenyl)borate,
triphenylphosphonium tetrakis(perfluorobiphenyl)borate,
triethylsilylium tetrakis(perfluorobiphenyl)borate,
benzene(diazonium) tetrakis(perfluorobiphenyl)borate,
trimethylammonium tetrakis(3,5-bis(trifluoromethyl)phenyl)borate,
triethylammonium tetrakis(3,5-bis(trifluoromethyl)phenyl)borate,
tripropylammonium tetrakis(3,5-bis(trifluoromethyl)phenyl)borate,
tri(n-butyl)ammonium tetrakis(3,5-bis(trifluoromethyl)phenyl)borate,
tri(t-butyl)ammonium tetrakis(3,5-bis(trifluoromethyl)phenyl)borate,
N,N-dimethylanilinium tetrakis(3,5-bis(trifluoromethyl)phenyl)borate,
N,N-diethylanilinium tetrakis(3,5-bis(trifluoromethyl)phenyl)borate,
N,N-dimethyl-(2,4,6-trimethylanilinium) tetrakis(3,5-bis(trifluoromethyl)phenyl)borate, tropillium tetrakis(3,5-bis(trifluoromethyl)phenyl)borate,
triphenylcarbenium tetrakis(3,5-bis(trifluoromethyl)phenyl)borate, triphenylphosphonium tetrakis(3,5-bis(trifluoromethyl)phenyl)borate,
triethylsilylium tetrakis(3,5-bis(trifluoromethyl)phenyl)borate,
benzene(diazonium) tetrakis(3,5-bis(trifluoromethyl)phenyl)borate,
and dialkyl ammonium salts such as:
di-(i-propyl)ammonium tetrakis(pentafluorophenyl)borate, and dicyclohexylammonium tetrakis(pentafluorophenyl)borate;
and additional tri-substituted phosphonium salts such as
tri(o-tolyl)phosphonium tetrakis(pentafluorophenyl)borate, and
tri(2,6-dimethylphenyl)phosphonium tetrakis(pentafluorophenyl)borate.

Most specifically, the ionic stoichiometric activator $(L-H)^{d+} (A^{d-})$ is
N,N-dimethylanilinium tetra(perfluorophenyl)borate,
N,N-dimethylanilinium tetrakis(perfluoronaphthyl)borate,
N,N-dimethylanilinium tetrakis(perfluorobiphenyl)borate,
N,N-dimethylanilinium tetrakis(3,5-bis(trifluoromethyl)phenyl)borate,
triphenylcarbenium tetrakis(perfluoronaphthyl)borate,
triphenylcarbenium tetrakis(perfluorobiphenyl)borate,
triphenylcarbenium tetrakis(3,5-bis(trifluoromethyl)phenyl)borate, or
triphenylcarbenium tetra(perfluorophenyl)borate.

Other examples of preferred ionizing activators include, [HNMe(C$_{18}$H$_{37}$)$_2^+$][B(C$_6$F$_5$)$_4$]; [HNPh(C$_{18}$H$_{37}$)$_2^+$][B(C$_6$F$_5$)$_4^-$] and [((4-n-Bu-C$_6$H$_4$)NH(n-hexyl)$_2$)$^+$][B(C$_6$F$_5$)$_4$] and [((4-n-Bu-C$_6$H$_4$)NH(n-decyl)$_2$)$^+$][B(C$_6$F$_5$)$_4$]. Specific preferred $(L-H)^+$ cations are N,N-dialkylanilinium cations, such as HNMe$_2$Ph$^+$, substituted N,N-dialkylanilinium cations, such as (4-n-Bu-C$_6$H$_4$)NH(n-C$_6$H$_{13}$)$_2^+$ and (4-n-Bu-C$_6$H$_4$)NH(n-C$_{10}$H21)$_2^+$ and HNMe(C$_{18}$H$_{37}$)$_2^+$. Specific examples of anions are tetrakis(3,5-bis(trifluoromethyl)phenyl)borate and tetrakis(pentafluorophenyl)borate.

In one embodiment, activation methods using ionizing ionic compounds not containing an active proton but capable of producing an active oligomerization catalyst are also contemplated. Such methods are described in relation to metallocene catalyst compounds in EP 0426637A1, EP 0573403A1 and U.S. Pat. No. 5,387,568, which are all herein incorporated by reference.

The process can also employ activator compounds that are initially neutral Lewis acids but form a cationic metal complex and a noncoordinating anion, or a zwitterionic complex upon reaction with the compounds of this invention. For example, tris(pentafluorophenyl) boron or aluminum may act to abstract a hydrocarbyl or hydride ligand to yield a cationic metal complex and stabilizing noncoordinating anion.

In another embodiment, the aforementioned activator compounds can also react with the compounds of the present invention to produce a neutral, uncharged catalyst capable of selective ethylene oligomerization. For example, Lewis acidic reagents such as, for example, alkyl or aryl aluminum or boron compounds, can abstract a Lewis basic ligand such as, for example, THF or Et$_2$O, from a compound yielding a coordinatively unsaturated catalyst capable of selective ethylene oligomerization.

When the cations of noncoordinating anion precursors are Brönsted acids such as protons or protonated Lewis bases (excluding water), or reducible Lewis acids such as ferrocenium or silver cations, or alkali or alkaline earth metal cations such as those of sodium, magnesium or lithium, the activator-to-catalyst-precursor molar ratio may be any ratio, however, useful ratios can be from 1000:1 to 1:1.

Combinations of two or more activators may also be used in the practice of this invention.

Another suitable ion forming, activator compounds comprise a salt of a cationic agent and a noncoordinating, compatible anion characterized by the general formula:

$$(X)^+(A^{d-})$$

X+ is a cationic agent capable of accepting/abstracting an anionic group; $A^{d-}$ is a non-coordinating anion having the charge d-; and d is an integer from 1 to 3.

Specific examples of $(X)^+$ include $R_3C^+$, $R_3Si^+$, $R_2Al^+$, where R is hydrocarbyl, substituted hydrocarbyl, halocarbyl, substituted halocarbyl, and halosubstituted-hydrocarbyl radicals. Specific examples include but are not limited to $Ph_3C^+$, $Et_3Si^+$, $(C_{18}H_{37})_2MeSi^+$, $Cp_2Al^+$.

Another suitable ion forming, activating cocatalyst comprises a salt of a cationic oxidizing agent and a noncoordinating, compatible anion characterized by the general formula: $(OX^{e+})_d(A^{d-})_e$ where $OX^{e+}$ is a cationic oxidizing agent having a charge of e+; e is an integer from 1 to 3; d is an integer from 1 to 3, and $A^{d-}$ is as previously defined. Examples of cationic oxidizing agents include: ferrocenium, hydrocarbyl-substituted ferrocenium, ammoniumyl $(R_3N^{+\cdot})$, $Ag^+$, or $Pb^{2+}$. Preferred embodiments of $A^{d-}$ are those anions previously defined with respect to the Bronsted acid containing activators, especially tetrakis(pentafluorophenyl)borate.

Specific examples of ammoniumyl groups include (p-Br—C$_6$H$_4$)$_3$N$^{+\cdot}$, (p-NO$_2$—C$_6$H$_4$)$_3$N$^{+\cdot}$, (p-F—C$_6$H$_4$)$_3$N$^{+\cdot}$, (p-Me-C$_6$H$_4$)$_3$N$^{+\cdot}$, (p-OMe-C$_6$H$_4$)$_3$N$^{+\cdot}$.

Group 13 Reagents, Divalent Metal Reagents, and Alkali Metal Reagents

Other general activators or compounds useful in an oligomerization reaction may be used. These compounds may be activators in some contexts, but may also serve other functions in the reaction system, such as alkylating a metal center or scavenging impurities. These compounds are within the general definition of "activator," but are not considered herein to be ion-forming activators. These compounds include a group 13 reagent that may be characterized by the formula $_{3-p}$D$_p$ where G$^{13}$ is selected from the group consisting of B, Al, Ga, In, and combinations thereof, p is 0, 1 or 2, each $R^{50}$ is independently selected from the group consisting of hydrogen, halogen, and optionally substituted alkyl, alkenyl, alkynyl, heteroalkyl, heteroalkenyl, heteroalkynyl, aryl, heteroaryl, and combinations thereof, and each D is independently selected from the group consisting of halogen, hydrogen, alkoxy, aryloxy, amino, mercapto, alkylthio, arylthio, phosphino and combinations thereof.

In other embodiments, the group 13 activator is an oligomeric or polymeric alumoxane compound, such as methylalumoxane and the known modifications thereof. See, for example, Barron, "Alkylalumoxanes, Synthesis, Structure and Reactivity", pp. 33-67 in Metallocene-Based Polyolefins: Preparation, Properties and Technology, J. Schiers and W. Kaminsky (eds.), Wiley Series in Polymer Science, John Wiley & Sons Ltd., Chichester, England, 2000, and references cited therein.

In other embodiments, a divalent metal reagent may be used that is characterized by the general formula $M'R^{50}_{2-p'}D_{p'}$ and p' is 0 or 1 in this embodiment and $R^{50}$ and D are as defined above. M' is the metal and is selected from the group consisting of Mg, Ca, Sr, Ba, Zn, Cd, Cu and combinations thereof.

In still other embodiments, an alkali metal reagent may be used that is defined by the general formula $M^{iv}R^{50}$ and in this embodiment $R^{50}$ is as defined above, and $M^{iv}$ is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula $SiR^{50}_{4-q}D_q$ where $R^{50}$ is defined as above, q is 1, 2, 3 or 4 and D is as defined above, with the proviso that at least one D is hydrogen.

Non-limiting examples of Group 13 reagents, divalent metal reagents, and alkali metal reagents useful as activators for the catalyst compounds described above include methyl lithium, butyl lithium, phenyl lithium, dihexylmercury, butylmagnesium, diethylcadmium, benzylpotassium, tri-n-butyl aluminum, diisobutyl ethylboron, diethylcadmium, and tri-n-amyl boron, and, in particular, the aluminum alkyls, such as hexyl-aluminum, ethyllaluminum, methylaluminum, and isobutyl aluminum, diisobutyl aluminum bromide, diethylaluminum chloride, ethylaluminum dichloride, isobutyl boron dichloride, methyl magnesium chloride, ethyl beryllium chloride, ethyl calcium bromide, diisobutyl aluminum hydride, methyl cadmium hydride, diethyl boron hydride, hexylberyllium hydride, dipropylboron hydride, octylmagnesium hydride, dichloroboron hydride, di-bromo-aluminum hydride and bromocadmium hydride. Other Group 13 reagents, divalent metal reagents, and alkali metal reagents useful as activators for the catalyst compounds described above are known to those in the art, and a more complete discussion of these compounds may be found in U.S. Pat. Nos. 3,221,002 and 5,093,415, which are herein fully incorporated by reference.

Other activators include those described in PCT publication WO 98/07515 such as tris(2,2',2"-nonafluorobiphenyl) fluoroaluminate, which publication is fully incorporated herein by reference. Combinations of activators are also contemplated by the invention, for example, alumoxanes and ionizing activators in combinations, see for example, EP 0573120B1, PCT publications WO 94/07928 and WO 95/14044 and U.S. Pat. Nos. 5,153,157 and 5,453,410, all of which are herein fully incorporated by reference.

Other suitable activators are disclosed in WO 98/09996, incorporated herein by reference, which describes activating bulky ligand metallocene catalyst compounds with perchlorates, periodates and iodates including their hydrates. WO 98/30602 and WO 98/30603, incorporated by reference, describe the use of lithium (2,2'-bisphenyl-ditrimethylsilicate)·4THF as an activator for a bulky ligand metallocene catalyst compound.

WO 99/18135, incorporated herein by reference, describes the use of organo-boron-aluminum activators. EP 078129981 describes using a silylium salt in combination with a non-coordinating compatible anion. Also, methods of activation such as using radiation (see EP 0615981B1 herein incorporated by reference), electro-chemical oxidation, and the like are also contemplated as activating methods for the purposes of rendering the chromium complexes or compositions active for the selective oligomerization of olefins. Other activators or methods are described in for example in U.S. Pat. Nos. 5,849,852, 5,859,653 and 5,869,723 and in WO 98/32775 and WO 99/42467 (dioctadecylmethylammonium-bis(tri(pentafluorophenyl)borane) benzimidazolide), which are herein incorporated by reference.

Additional optional activators include metal salts of non-coordinating or weakly coordinating anions, for example where the metal is selected from Li, Na, K, Ag, Ti, Zn, Mg, Cs, and Ba.

Co-Activator

Preferably the co-activator is an organoaluminium compound and/or an organoboron compound. Alternatively it may be an organic salt such as methyl lithium and/or methyl magnesium bromide, or an inorganic acid or salt such as tetrafluoroboric acid etherate, silver tetrafluoroborate, sodium hexafluoroantimonate, and the like.

Examples of suitable organoboron compounds are boroxines, triethylborane, tris(pentafluoropheny)borane, tributyl borane and the like.

Suitable organoaluminium compounds include compounds of the formula $Al(R^9)_3$ ($R^9$ being the same or different), where each $R^9$ is independently an organyl group, a halogenated organyl group or a halide, with at least one of $R^9$ being an organyl group or a halogenated organyl group. Examples include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, and aluminoxanes.

Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Mixtures of different aluminoxanes may also be used in the process.

In an embodiment of the invention the co-activator may comprise a compound of the formula

wherein

M' is selected from the group consisting of a group 3A atom, a group 4A atom and a metal atom, including an alkali metal atom and an alkaline earth metal atom;

n is 1 or a larger integer; and

R' is an organic group, R being the same or different when n is larger than 1.

Preferably M' is selected from the group consisting of a group 3A atom, a group 4A atom, and a transition metal atom. Preferably the R group is bound to a group 3A atom. Preferably the group 3A atom is selected from the group consisting of Al and B, preferably it is Al.

The organic group R may be an organyl group, and preferably it comprises a hydrocarbyl group, preferably it comprises an alkyl group, preferably methyl, ethyl or a larger alkyl group.

In one embodiment of the invention the co-activator comprises $AlR''_3$ wherein R" is an alkyl group.

The co-catalyst may be selected from the group consisting of trimethylaluminium (TMA); triethylaluminium (TEA), tributylaluminium, tri-isobutylaluminium (TIBA) and tri-n-octylaluminium.

It will be appreciated that TMA is relatively expensive and accordingly the use thereof may be wished to be avoided. It has been found that by using an activator as defined in the present invention in combination with a co-activator as defined above (but excluding MAO) the use of TMA can be avoided as a co-catalyst.

It is foreseen that a co-activator as defined hereinabove will usually be used in combination with an activator as defined above.

In use, where both an activator and a co-activator are used, the co-activator may be added first and the activator may be added subsequently.

Zinc Compound

An additive can be used in the form of a zinc-containing species. The species can be any form of zinc or any zinc containing compound. The zinc compound may undergo reaction in situ with the trialkylaluminium to form a new zinc species in situ.

Specific examples of suitable zinc compounds include zinc, activated zinc, zinc halides, zinc alkyls, zinc oxygenates (including zinc acetate, acetylacetonates and carboxylates) and zinc porphyrin. Preferably, the zinc compound is zinc dialkyl, most preferably dimethyl zinc or diethyl zinc.

The zinc compound is present in the reaction of the invention in a sufficient quantity such that the ratio of the molar amount of zinc in the zinc compound to the molar amount of chromium in the source of chromium is between 1 and 10000, preferably between 10 and 1000, and more preferably between 50 and 450.

The zinc may be used as any concentration of stock solution and the concentration in situ in the reactor should be between 0.0001 mmol/L and 1 mol/L, more preferably between 0.001 mmol/L and 0.1 mol/L, and most preferably between 0.01 mmol/L and 0.01 mol/L.

The zinc compound may be added at any stage during the activation process, most preferably it is added directly to the reactor. The zinc may be used as a mixed stock solution with the trialkylaluminium, or with any other component.

The Applicant has found that the use of the zinc compound in conjunction with the activator compound significantly reduces the level of solids/polymer formed as by-product during the oligomerisation reaction.

Olefinic Compound to be Oligomerised

The olefinic compound may comprise a single olefinic compound or a mixture of olefinic compounds. In one embodiment of the invention it may comprise a single olefin.

The olefin may include multiple carbon-carbon double bonds, but preferably it comprises a single carbon-carbon double bond. The olefin may comprise an a-olefin with 2 to 30 carbon atoms, preferably 2 to 10 carbon atoms. The olefinic compound may be selected from the group consisting of ethylene, propene, 1-butene, 1-pentene, 1-hexene, 1-heptene, and 1-octene, 1-nonene, 1-decene, 3-methyl-1-pentene, 3-methyle-1-penetene, 4-methyl-1-pentene, styrene, p-methyl styrene, 1-dodecene or combinations thereof. Preferably, it comprises ethylene or propene, preferably ethylene. The ethylene may be used to produce hexene and/or octene, preferably 1-hexene and/or 1-octene.

Oligomerisation

The oligomerisation process may comprise a trimerisation process, alternatively or additionally it may comprise a tetramerisation process.

The process may be oligomerisation of two or more different olefinic compounds to produce an oligomer containing the reaction product of the two or more different olefinic compounds. Preferably however, the oligomerisation (preferably trimerisation and/or tetramerisation) comprises the oligomerisation of a single monomer olefinic compound.

In one preferred embodiment of the invention the oligomerisation process is oligomerisation of a single α-olefin to produce an oligomeric α-olefin. Preferably it comprises the trimerisation and/or tetramerisation of ethylene, preferably to 1-hexene and/or 1-octene.

Oligomeric Product

The oligomeric product may be an olefin, or a compound including an olefinic moiety. Preferably the oligomeric product includes an olefin, more preferably an olefin containing a single carbon-carbon double bond, and preferably it includes an a-olefin. The olefin product may include hexene, preferably 1-hexene, but more preferably it includes octene, preferably 1-octene. In a preferred embodiment of the invention the olefinic product includes a mixture of hexene and octene, preferably a mixture of 1-hexene and 1-octene.

In one preferred embodiment of the invention the oligomerisation process is a selective process to produce an oligomeric product containing more than 30% by mass of a single olefin product. The olefin product may be hexene, preferably 1-hexene, but alternatively it may be octene, preferably 1-octene.

Preferably the product contains at least 35% of the said olefin, preferably α-olefin, but it may be more than 40%, 50%, or even 60% by mass.

The olefinic product may be branched, but preferably it is non-branched.

Catalyst Preparation

It is foreseen that i) the source of chromium and ii) the ligating compound (referred to in (a) of the main statement of the invention) may be first reacted together and the resulting product may even be isolated, before combining it with the catalyst activator iii). However, i), ii) and iii) may be combined in any suitable order in the presence or absence of a solvent, but preferably at least some, but preferably all of i), ii) and iii) are first combined and subsequently contacted with the olefinic compound.

The contacting of the olefinic compound with compounds i) to iii) and b) preferably takes place under conditions to allow oligomerisation of the olefinic compound. These conditions are well known to a person skilled in the art and include elevated temperatures and pressure. The solid oligomerisation may be carried out at temperatures from 100° C. to 250° C., but temperatures in the range of 15° C. to 130° C. are preferred, particularly temperatures in the range from 50° C. to 120° C. Oligomerisation is preferably carried out at a temperature of at least 0° C., preferably at least 40° C., and preferably at least 50° C. Preferably it is carried out at a pressure of at least 100 kPa, preferably at least 1000 kPa, preferably at least 3000 kPa.

The preparation of the activated catalyst may be carried out in a liquid medium, preferably an inert liquid medium. The liquid medium may be the same liquid medium wherein the oligomerisation with the diluted catalyst is carried out.

The activated oligomerisation catalyst before dilution may be prepared in the same container as the one in which the diluted activated oligomerisation catalyst is contacted with the olefinic compound to be oligomerised. Preferably the activated oligomerisation catalyst before dilution is prepared in a separate container as the one in which the oligomerisation catalyst is contacted with the olefinic compound to be oligomerised.

The source of chromium and ligating compound may be combined to provide any suitable molar ratio, preferably a chromium to ligand compound molar ratio, from about 0.01:100 to 10 000:1, preferably from about 0.1:1 to 10:1.

The zinc can be used in any loading compared to the chromium, preferably between 1 and 10000, more preferably between 10 and 1000, most preferably between 50 and 450. The zinc can be used as any concentration of stock solution and the concentration in situ in the reactor can be between 0.0001 mmol/L and 1 mol/L, more preferably between 0.001 mmol/L and 0.1 mol/L, most preferably between 0.01 mmol/L and 0.01 mol/L.

The zinc additive can be added at any stage during the activation procedure, most preferably it is added directly to the reactor. The zinc can be used as a mixed stock solution with the trialkylaluminium.

The process may also include combining one or more different sources of chromium with one or more different ligating compounds.

The oligomerisation catalyst or its individual components, in accordance with the invention, may also be immobilised by supporting it on a support material, for example, silica, alumina, $MgCl_2$, zirconia, artificial hectorite or smectorite clays such as Laponite™ RD or mixtures thereof, or on a polymer, for example polyethylene, polypropylene, polystyrene, or poly(aminostyrene). The catalyst can be formed in situ in the presence of the support material, or the support can be pre-impregnated or premixed, simultaneously or sequentially, with one or more of the catalyst components or the oligomerisation catalyst. In some cases, the support material can also act as a component of the activator. This approach would also facilitate the recovery of the catalyst from the reaction mixture for reuse.

The invention will now be described, by way of non-limiting examples:

EXAMPLES

In this specification the abbreviation TEA is used for triethylaluminium and PNP is used for bis(diarylphosphanyl)amine ligand A 1 or 1.2 L stainless steel reactor was heated to 120° C. under vacuum for 30 minutes, cooled to 60° C. and back-filled with Ar. The reactor was charged with solvent and saturated with ethylene.

Separately, TEA then activator salt (as stock solutions) were added sequentially to a stirred solution of $Cr(^tBu_2acac)_3$/PNP. The activation solution was added to the reactor and the reactor was pressurized to 50 bar with ethylene. The reaction pressure was kept constant through addition of ethylene monitored via a flow-meter. After cessation of ethylene uptake, the gas supply was closed and the reactor cooled to 0° C. Excess ethylene was bled and the reactor contents treated sequentially with 1000 μL of nonane (GC internal standard), MeOH and 10% HCl (aq). A sample of the organic phase was taken for GC-FID analysis. Any solid formed was collected, washed repeatedly with 10% HCl (aq.) and EtOH, dried overnight and weighed.

Example 1

Oligomerisation of Ethylene Using a System Based on Cr/PNP/[$(C_{18}H_{37})_2$N(H)(Me)][B$(C_6F_5)_4$]/TEA In all tests using this reagent the total amount of $ZnEt_2$ was added to the reactor with the solvent at the pre-scrub stage. All catalysis has been conducted on the 1.2 L rig where typical runs consume >400 g of ethylene, thus the absolute amount of polymer formed is roughly 1-3 g. Given the ability to collect, wash, dry and weigh the polymer to the nearest 10 mg, the accuracy of the polymer quantification is better than 0.0025%.

Table 1 below shows against entry #316 a standard run using Cr/PNP/TEA/borate in PhCl; the total solid polymer formation is 0.65% polymer.

In contrast, entry 330 shows a run using the same conditions except with an additional 420 eq. of $ZnEt_2$. It can be seen that the total solids formation is reduced to 0.38%—representing a 42% reduction in polymer formation.

Entry 312 is a borate run in the aliphatic solvent cyclohexane, included for comparison; the polymer formation is 0.57%. As can be seen from entries 354 (25 eq.), 346 (50 eq.), 345 (100 eq.), 73 (150 eq.), 348 (420 eq.), addition of $ZnEt_2$ at 50 equivalents or above successfully reduces the level of polymer formation to an average of 0.35%—an average reduction of 35%. Entries 234 (1000 eq), 237 (5000 eq) and 238 (10000 eq) all show that even at high zinc loadings the level of polymer is reduced, whilst maintaining good activity.

Entry 239 is a borate run in the aliphatic solvent cyclohexane with a different ligand and chromium source, included for comparison; the polymer formation is 0.78%. As can be seen from entries 236 (1 eq.) and 235 (10 eq.), addition of $ZnEt_2$ even at these very low loadings, successfully reduces the level of polymer formation to an average of 0.45%.

Entry 324 is a run performed in 2,2,4-trimethylpentane (IMP) which shows a polymer formation level of 0.92%. Runs 347 and 332 show that addition of 50 and 420 eq of $ZnEt_2$ can reduce this polymer level to an average of 0.46%.

Looking at all examples in Table 1 it can be seen that the addition of $ZnEt_2$ has little or no effect upon the amount of 1-hexene and 1-octene formed.

TABLE 1

Results of catalyst testing with varying amounts of diethyl zinc.

| Entry # | Solvent | $ZnEt_2$ Eq. | Cat. Time (min) | Activity g/gCr/h | Hexene and octene wt %[b] | Polymer wt %[c] (g) |
|---|---|---|---|---|---|---|
| 316 | PhCl | 0 | 75.3 | 5,214,575 | 83.2 | 0.65 (2.63) |
| 330 | PhCl | 420 | 43.3 | 9,081,307 | 82.0 | 0.38 (1.49) |
| 312 | CyH | 0 | 86.0 | 4,549,445 | 81.9 | 0.57 (2.41) |
| 239[e] | CyH | 0 | 154 | 1,786,201 | 87.5 | 0.78 (2.34) |
| 236[e] | CyH | 1 | 111.6 | 2,935,441 | 85.6 | 0.43 (1.53) |
| 235[e] | CyH | 10 | 87.1 | 3,670,522 | 86.5 | 0.46 (1.59) |
| 354 | CyH | 25 | 85.3 | 4,133,342 | 82.3 | 0.37 (1.41) |
| 346 | CyH | 50 | 97.0 | 3,733,376 | 82.5 | 0.31 (1.22) |
| 345 | CyH | 100 | 94.5 | 4,046,426 | 81.6 | 0.47 (1.96) |

TABLE 1-continued

Results of catalyst testing with varying amounts of diethyl zinc.

| Entry # | Solvent | ZnEt$_2$ Eq. | Cat. Time (min) | Activity g/gCr/h | Hexene and octene wt %$^b$ | Polymer wt %$^c$ (g) |
|---|---|---|---|---|---|---|
| 73 | CyH | 150 | 112.6 | 3,469,238 | 83.4 | 0.25 (1.08) |
| 348 | CyH | 420 | 94.6 | 3,774,950 | 83.3 | 0.37 (1.45) |
| 234$^e$ | CyH | 1000 | 99.6 | 3,161,004 | 86.8 | 0.45 (1.54) |
| 237$^e$ | CyH | 5000 | 120.0 | 2,291,502 | 87.0 | 0.32 (0.95) |
| 238$^e$ | CyH | 10000 | 224.0 | 1,014,743 | 87.4 | 0.21 (0.52) |
| 324 | TMP | 0 | 114.2 | 3,531,036 | 82.2 | 0.92 (4.01) |
| 347 | TMP | 50 | 154.7 | 2,407,089 | 81.2 | 0.47 (1.89) |
| 332 | TMP | 420 | 232.0 | 1,660,724 | 82.1 | 0.44 (1.77) |

General conditions:
$^a$1.25 μmol Cr($^t$Bu$_2$acac)$_3$; 1.2 eq. Ph$_2$P—N{C(H)(Me)({CH$_2$}$_5$CH$_3$)}—PPh$_2$; 1.2 eq. [(C$_{18}$H$_{37}$)$_2$N(H)(Me)][B(C$_6$F$_5$)$_4$]$^-$$_2$; 420 eq. TEA (50 eq. activation, 370 eq. reactor); p(=) 50 bar 60° C.; 200 mL solvent; 1.2 L rig.
$^b$= % of liquid fraction
$^c$= % of total product formed (liquid and solid).
$^e$1.25 μmol Cr(2-EH)$_3$; 1.2 eq. Ph$_2$P—N{C(H)Me(C(H)(Me){CH$_2$}$_4$CH$_3$)}—PPh$_2$

Example 2

Oligomerisation of Ethylene Using a System Based on MAO

For this study, catalysis was either performed in cyclohexane or in 2,2,4-trimethylpentane. Catalyst activity and product selectivity data is summarised in Table 2. The polymeric product made in catalysis was carefully isolated, repeatedly washed and dried.

Entry 056 represents the optimum MAO activated catalysis that can be achieved in CH for the two sets of precatalysts and entry 181 for catalysis in 2,2,4-trimethylpentane. Diethyl or dimethyl zinc is added to the reactor in the normal "pre-scrub phase", which immediately follows solvent addition to the reactor.

Catalyst performance is shown for the standard run that contains 50 eq. of diethyl zinc (entry 059), and is further accompanied by a noteworthy reduction in solids (from 0.8% to 0.6%). Diethyl zinc again appears to have little effect on the total selectivity of the catalyst; entry 056 (83.5%) versus 059 (83.9%).

Although a clear activity enhancement is seen when 50 eq of ZnMe$_2$ is used (entry 185), there is no reduction in solids. However, increasing the equivalents from 50 to 100 shows a reduction from 0.49 to 0.41% as well as a significant increase in activity.

TABLE 2

The effect of ZnR$_2$ R = Me or Et on MMAO catalysis.

| Entry (eq. ZnEt$_2$) | Productivity g/gCr | Activity g/gCr/H | Hexene and octene wt %$^b$ | Pol wt % (g)$^c$ |
|---|---|---|---|---|
| 056$^a$ (0 eq. ZnEt$_2$) | 3446895 | 1969654 | 80.7 | 0.80 (2.83) |
| 058$^a$ (100 eq. ZnEt$_2$) | 2476986 | 1170230 | 82.4 | 0.60 (1.49) |
| 059$^a$ (50 eq. ZnEt$_2$) | 3298861 | 1691724 | 83.9 | 0.60 (1.49) |
| 181$^d$ (0 eq. ZnMe$_2$) | 1805992 | 2642916 | 87.1 | 0.49 (0.92) |
| 190$^d$ (100 eq. ZnMe$_2$) | 1899827 | 3864054 | 86.8 | 0.41 (0.81) |

General conditions:
$^a$2.0 μmol Cr(acac)$_3$ and 1.2 eq. Ph$_2$P—N{C(H)(Me)({CH$_2$}$_2$CH$_3$)}—PPh$_2$; MAO (480 eq.); 50 bar ethylene; 60° C.; 200 mL cyclohexane.
$^b$= % of liquid fraction
$^c$= % of total product formed (liquid and solid)
$^d$2.0 μmol Cr(acac)$_3$ and 1.1 eq. Ph$_2$P—N{C(H)(Me)($^i$Pr)}—PPh$_2$ in 2,2,4-trimethylpentane; MAO (480 eq.); 45 bar ethylene; 60° C.; 300 mL.

Example 3

Change in Conditions

The results reflected in Table 3 below show that the effect of adding ZnEt$_2$ is not affected by the choice of chromium source and co-catalysts used. This effect is also not unique to the PNP ligand system as not only does it work with Ph$_2$P—N{C(H)(Me)($^i$Pr)}—PPh$_2$, Ph$_2$P—N{C(H)(Me)({CH$_2$}$_5$CH$_3$)}—PPh$_2$, and the bulky (o-Me-C$_6$H$_4$)$_2$P—N($^i$Pr)—PPh$_2$ ligands but also with other ligands such as Ph$_2$P—N(Me)-N—(CH$_2$CH$_2$Pr$^i$)—P, bis(diphenylphosphanyl)ethane (DPPE) and bis(diphenylphosphanyl)methane (DPPM). This indicates that the effect of ZnEt$_2$ is not exclusive to tetramerisation systems PNP, PNNP, and DPPE but also, as expected, applies to unselective oligomerisation systems, DPPM. The most significant change in the use of ZnEt$_2$ comes upon running in alternative solvents.

TABLE 3

Results of catalyst testing with varying conditions.

| Entry # | Cr/L/A$^f$ | ZnEt$_2$ Eq. | Cat. Time (min) | Activity g/gCr/h | Hexene and octene wt %$^d$ | Polymer wt %$^c$ (g)$^e$ |
|---|---|---|---|---|---|---|
| 424 | Cr($^t$Bu$_2$acac)$_3$/ Ph$_2$P—N{C(H)(Me)({CH$_2$}$_5$CH$_3$)}—PPh$_2$/ OAB | 0 | 207.0 | 1,744,506 | 83.0 | 0.85 (3.34) |
| 423 | Cr($^t$Bu$_2$acac)$_3$/ Ph$_2$P—N{C(H)(Me)({CH$_2$}$_5$CH$_3$)}—PPh$_2$/ OAB | 420 | 151.5 | 2,469,579 | 82.4 | 0.77 (3.12) |

TABLE 3-continued

Results of catalyst testing with varying conditions.

| Entry # | Cr/L/A[f] | ZnEt$_2$ Eq. | Cat. Time (min) | Activity g/gCr/h | Hexene and octene wt %[d] | Polymer wt %[c] (g)[e] |
|---|---|---|---|---|---|---|
| 427 | Cr(acac)$_3$/<br>Ph$_2$P—N{C(H)(Me)({CH$_2$}$_2$CH$_3$)}—PPh$_2$/<br>TA | 0 | 39.9 | 9,962,823 | 84.1 | 1.76 (7.55) |
| 426 | Cr(acac)$_3$/<br>Ph$_2$P—N{C(H)(Me)({CH$_2$}$_2$CH$_3$)}—PPh$_2$/<br>TA | 420 | 49.6 | 8,718,296 | 83.2 | 0.38 (1.79) |
| 434[c] | Cr($^t$Bu$_2$acac)$_3$/<br>Ph$_2$P—N{C(H)(Me)({CH$_2$}$_5$CH$_3$)}—PPh$_2$/<br>RB | 0 | 135.0 | 2,874,486 | 83.1 | 2.36 (9.93) |
| 435[c] | Cr($^t$Bu$_2$acac)$_3$/<br>Ph$_2$P—N{C(H)(Me)({CH$_2$}$_5$CH$_3$)}—PPh$_2$/<br>RB | 100 | 89.6 | 3,530,896 | 83.8 | 1.85 (6.35) |
| 445[b] | Cr(2-EH)$_3$/<br>DPPE/<br>RB | 0 | 74.0 | 115,961 | 70.5 | 24.7 (4.59) |
| 446[b] | Cr(2-EH)$_3$/<br>DPPE/<br>RB | 100 | 107.0 | 147,931 | 71.1 | 13.0 (4.44) |
| 447[b] | Cr(2-EH)$_3$/<br>DPPM/<br>RB | 0 | 95.7 | 17,092 | 28.8 | 77.9 (2.76) |
| 448[b] | Cr(2-EH)$_3$/<br>DPPM/<br>RB | 100 | 107.2 | 16,159 | 27.9 | 66.2 (2.48) |
| 452[b] | Cr(2-EH)$_3$/<br>(o-Me—C$_6$H$_4$)$_2$P—N($^i$Pr)—PPh$_2$/<br>RB | 100 | 49.5 | 632,715 | 91.0 | 4.94 (1.67) |
| 453[b] | Cr(2-EH)$_3$/<br>(o-Me—C$_6$H$_4$)$_2$P—N($^i$Pr)—PPh$_2$/<br>RB | 0 | 18.0 | 443,168 | 91.0 | 23.02 (1.99) |
| 454[b] | Cr(2-EH)$_3$/<br>Ph$_2$P—N(Me)—N—(CH$_2$CH$_2$Pr$^i$)—PPh$_2$/<br>RB | 100 | 51.5 | 441,991 | 90.2 | 11.47 (2.83) |
| 455[b] | Cr(2-EH)$_3$/<br>Ph$_2$P—N(Me)—N—(CH$_2$CH$_2$Pr$^i$)—PPh$_2$/<br>RB | 0 | 65.8 | 80,240 | 86.9 | 61.88 (3.54) |
| 428 | Cr($^t$Bu$_2$acac)$_3$/<br>Ph$_2$P—N{C(H)(Me)({CH$_2$}$_5$CH$_3$)}—PPh$_2$/<br>RB | 420 ZnMe$_2$ | 80.3 | 4,044,548 | 83.9 | 0.43 (1.50) |

General conditions:
[a] 1.25 µmol Cr; 1.2 eq. Ligand; 1.2 eq. Anion; 420 eq. TEA (50 eq. activation, 370 eq.; 200 mL solvent 1.2 L reactor p(=) 50 bar; 60° C.; 200 mL solvent; 1.2 L rig.
[b] 150 eq. TEA (activation) 65 mL solvent 300 mL reactor.
[c] Al$^i$Bu$_3$ in place of TEA.
[d] = % of liquid fraction
[e] = % of total product formed (liquid and solid).
[f] OAB = [Oct$_3$NH][B(C$_6$F$_5$)4]; RB = [(C$_{18}$H$_{37}$)$_2$N(H)Me][B(C$_6$F$_5$)$_4$]; TA = [Ph$_3$C][Al(O$^t$Bu$^F$)$_4$]; Cr(2-EH)$_3$ = Cr(2-ethylhexanoate)$_3$; DPPE = bis(diphenylphosphanyl)ethane; DPPM = bis(diphenylphosphanyl)methane.

The use of zinc alkyl, in particular diethyl zinc in conjunction with the Cr/PNP/TEA/borate catalyst system and dimethyl zinc in conjunction with the Cr/PNP/MMAO system clearly has benefits in reducing the level of polymer formation by a significant amount, whilst increasing the rate of catalysis.

It is further noted that only a low level of ZnEt$_2$ is required to achieve this effect, circa 50-100 equivalents, with higher loadings of Zn offering little further advantage.

The use of this reagent also fulfils the requirement on having little or no effect upon the selective oligomerisation mechanism with little perturbation in the total target oligomer value being observed.

The invention claimed is:

1. A process for producing an oligomeric product by oligomerisation of at least one olefinic compound, the process including:

a) providing an activated oligomerisation catalyst by combining, in any order,
  i) a source of chromium;
  ii) a ligating compound of the formula I

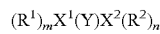

$$(R^1)_m X^1(Y)X^2(R^2)_n \quad \quad I$$

wherein: X$^1$ and X$^2$ are independently an atom selected from the group consisting of nitrogen, phosphorus, arsenic, antimony, bismuth, oxygen, sulphur and selenium or said atom oxidized by S, Se, N or O where the valence of X$^1$ and/or X$^2$ allows for such oxidation;
Y is a linking group between X$^1$ and X$^2$;
m and n are independently 0, 1 or a larger integer; and
R$^1$ and R$^2$ are independently hydrogen, a hydrocarbyl group, an organoheteryl group or a heterohydrocarbyl group, and R being the same or different when m>1, and R$^2$ being the same or different when n>1;
  iii) a catalyst activator or combination of catalyst activators;

b) providing a zinc compound; and
c) contacting the at least one clef irk compound with a composition containing the activated oligomerisation catalyst and the zinc compound, the zinc compound being present in a sufficient quantity such that the ratio of the molar amount of zinc in the zinc compound to the molar amount of chromium in the source of chromium is from 10 to 1000.

2. A process for activating an oligomerisation catalyst to be used to produce an oligomeric product from at least one olefinic compound, the process comprising the combination, in any order, of
i) a source of chromium;
ii) a ligating compound of the formula I $$(R^1)_m X^1 (Y) X^2 (R^2)_n \quad \quad I$$

wherein: $X^1$ and $X^2$ are independently an atom selected from the group consisting of nitrogen, phosphorus, arsenic, antimony, bismuth, oxygen, sulphur and selenium or said atom oxidized by S, Se, N or O where the valence of $X^1$ and/or $X^2$ allows for such oxidation;
Y is a linking group between $X^1$ and $X^2$;
m and n are independently 0, 1 or a larger integer; and
$R^1$ and $R^2$ are independently hydrogen, a hydrocarbyl group an organoheteryl group or a heterohydrocarbyl group, and $R^1$ being the same or different when m>1 and $R^2$ being the same or different when n>1;
iii) a catalyst activator or combination of catalyst activators;
iv) a zinc compound, the zinc compound being present in a sufficient quantity such that the ratio of the molar amount of zinc in the zinc compound to the molar amount of chromium in the source of chromium is from 10 to 1000.

3. The process of claim 1 or claim 2 wherein the zinc compound is present in a sufficient quantity such that the ratio of the molar amount of zinc in the zinc compound to the molar amount of chromium in the source of chromium is from 50 to 450.

4. The process of claim 1 or claim 2 wherein the process includes the use of a solvent.

5. The process of claim 1 or claim 2 wherein the oligomerisation catalyst is a trimerisation catalyst or a tetramerisation catalyst.

6. The process of claim 1 or claim 2 wherein $X^1$ and $X^2$ are independently phosphorus or phosphorus oxidised by S or Se or N or O.

7. The process of claim 1 or claim 2 wherein the ligating compound is of the formula II

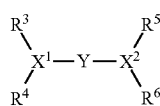

wherein Y is a linking group between $X^1$ and $X^2$, $X^1$ and X2 are independently selected from the group consisting of nitrogen, phosphorus, arsenic, antimony and bismuth and $R^3$ to $R^6$ are each independently a hydrocarbyl group or a heterohydrocarbyl group.

8. The process of claim 1 or claim 2 wherein Y is selected from the group consisting of an organic linking group comprising a hydrocarbylene, substituted hydrocarbylene, heterohydrocarbylene and a substituted heterohydrocarbylene; an inorganic linking group comprising either a single- or two-atom linker spacer; and a group comprising methylene; dimethylmethylene; ethylene; ethene-1,2-diyl; propane-1,2-diyl, propane-1,3-diyl; cyclopropane-1,1-diyl; cyclopropane-1,2-diyl; cyclobutane-1,2-diyl, cyclopentane-1,2-diyl, cyclohexane-1,2-diyl, cyclohexane-1,1-diyl; 1,2-phenylene; naphthalene-1,8-diyl; phenanthrene-9,10-diyl, phenanthrene-4,5-diyl, 1,2-catecholate, 1,2-diarylhydrazine-1,2-diyl (—N(Ar)—N(Ar)-) where Ar is an aryl group; 1,2-dialkylhydrazine-1,2-diyl (—N(Alk)-N(Alk)-) where Alk is an alkyl group; —B($R^7$)—, —Si($R^7$)$_2$—, —P($R^7$)— and —N($R^7$)— where $R^7$ is hydrogen, a hydrocarbyl or heterocarbyl or halogen.

9. The process of claim 7 wherein the ligating compound is of the formula III

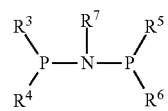

wherein $R^3$ to $R^7$ are each independently a hydrocarbyl group or a heterohydrocarbyl group.

10. The process of claim 9 wherein each of $R^3$ to $R^6$ is an alkyl selected from the group consisting of methyl, ethyl and isopropyl or an aromatic selected from the group consisting of phenyl and substituted phenyl.

11. The process of claim 1 or claim 2 wherein the activator is selected from the group of organoboron compound, alumoxanes including modified aluminoxanes, aluminum alkyls, other metal or main group alkyl or aryl compounds, ionizing activators which are neutral or ionic, Lewis acids, reducing acids oxidising agents and combinations thereof.

12. The process of claim 1 or claim 2 wherein the process includes a reagent selected from a Group 13 reagent, a divalent metal reagent or an alkali metal reagent.

13. The process of claim 1 or claim 2 wherein the zinc compound is selected from zinc, activated zinc, and zinc-containing compounds selected from the group comprising zinc halides, zinc alkyls, zinc oxygenates including zinc acetate, zinc acetylacetonates and zinc carboxylates, and zinc porphyrin.

14. The process of claim 13 wherein the zinc-containing compound is a zinc dialkyl.

15. The process of claim 14, wherein the in dialkyl is dimethyl zinc or diethyl zinc.

* * * * *

UNITED STATES PATENT AND TRADEMARK OFFICE
CERTIFICATE OF CORRECTION

PATENT NO. : 8,859,696 B2
APPLICATION NO. : 13/502664
DATED : October 14, 2014
INVENTOR(S) : Hanton et al.

It is certified that error appears in the above-identified patent and that said Letters Patent is hereby corrected as shown below:

In the Claims

Claim 1, Col. 26, Line 64, "R" should read as --$R^1$--.

Claim 1, Col. 26, Line 64, "m>1" should read as --n>1--.

Claim 1, Col. 27, Line 2, "clef irk" should read as --olefinic--.

Claim 7, Col. 28, Line 1, "X2" should read as --$X^2$--.

Signed and Sealed this
Seventeenth Day of February, 2015

Michelle K. Lee
*Deputy Director of the United States Patent and Trademark Office*